United States Patent [19]

Geacintov et al.

[11] Patent Number: 5,055,485
[45] Date of Patent: Oct. 8, 1991

[54] INACTIVATION OF VIRUSES IN CELL- AND PROTEIN-CONTAINING COMPOSITIONS USING ARYL DIOL EPOXIDES

[75] Inventors: Nicholas E. Geacintov; Jay E. Valinsky, both of New York; Bolanle Williams, Forest Hills; Bernard Horowitz, New Rochelle, all of N.Y.

[73] Assignee: New York Blood Center, Inc., New York, N.Y.

[21] Appl. No.: 279,179

[22] Filed: Dec. 2, 1988

[51] Int. Cl.$^5$ ............................................. A61K 31/335
[52] U.S. Cl. ........................................ 514/449; 435/1; 435/2; 514/2; 424/529; 424/530; 424/531; 424/583
[58] Field of Search ........................ 435/1, 2; 514/449

[56] References Cited

PUBLICATIONS

Yagi et al. J. Am. Ch. Soc. vol. 99(1977) pp. 1604–1611.
Wislocki et al.—Cancer Research vol. 36 Sep. 1976 pp. 3350–3357.
Wood et al.—Cancer Research vol. 36 (Sep. 1976) pp. 3358–3366.

*Primary Examiner*—Sam Rosen
*Attorney, Agent, or Firm*—Sprung Horn Kramer & Woods

[57] ABSTRACT

A process of inactivating infectious viruses in a cell-containing or a protein-containing composition containing such viruses, comprising contacting such composition with an effective amount of at least one aryl diol epoxide of the formula

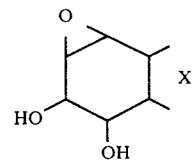

in which
  X is an aromatic ring system having from 3 to 6 used rings, for a sufficient period of time substantially to inactivate said viruses without incurring substantial disruption or inactivation of cells or without incurring substantial protein denaturation.

15 Claims, No Drawings

INACTIVATION OF VIRUSES IN CELL- AND PROTEIN-CONTAINING COMPOSITIONS USING ARYL DIOL EPOXIDES

BACKGROUND OF THE INVENTION

1. Field of the Invention

This invention relates to producing virus-free biological mixtures such that valuble biological components, e.g., cells and proteins, retain their structure and function. More especially, this invention relates to the inactivation of viruses, e.g., hepatitis viruses, human immunodeficiency viurus (HIV), or other virues in human blood, blood cellular components, blood plasma and blood plasma fractions such that each remains suitable for therapeutic use. In particular, this invention relates to producing cellular blood products (e.g., whole blood, red cell concentrates, platelet concentrates and leukoiyte concentrates) and non cellular blood products (e.g., whole plasma, antihemophilic factor immune globulin, fibrinogen) which are rendered substantiàlly free of infectious hepatitis B virus, non-A, non-B hepatitis virus, or other viral infectivity by treatment with aryl diol epoxides.

2. Background Information

Transmission of viral diseases (e.g., hepatitis B, acquired immunodeficiency syndrome, cytomegalovirus infections) through blood transfusion is a significant problem in transfusion medicine. While donor selection criteria and screening of donor blood for viral markers helps reduce the transmission of viruses to recipients, screening methods are incomplete, and it is desirable to inactivate viruses contained in donor blood without altering the structure and function of its valuable consitituents, e.g., red blood cells, platelets, leukocytes, and plasma proteins. Similarly, other biological mixtures, e.g., hybridoma cell lines, milk and sperm, can contain infections virus and it would be advantageous to inactivate said virus(es) while retaining the valuable consitutents of these mixtures.

Methods typically used for the inactivation viruses, such as those useful in the preparation of viral vaccines, generally destroy the function and structure of cells and proteins. For instance, in the preparation of a hepatitis B virus vaccine, it is common practice to heat the prearation at temperatures in excess of 80° C. and to treat with formaldehyde. These treatments not only inactivate viral infectivity, but also irreversibly damage blood cells and proteins, rendering them unsuitable for transfusion.

Recently, both physical and chemical methods have been developed which inactivate viruses contained in blood, while retaining blood protein structure and function. Protein solutions heated either following lyophilization or in solution in the presence of high concentrates of sugars and/or amino acids have been shown to have greatly reduced viral infectivity, while retaining functional activity of many proteins. Chemical methods in use for the preparation of protein mixtures include beta-propiolactone and the use of solvent/detergent mixtures, especially tri(n-butyl)-phosphate. However, application of these methods to cells generally results in disruption and inactivation.

As a result of the foregoing, viral inactivation methods are not commonly applied to the preparation of whole blood and blood cell components derived therefrom. Rather, viral safety relies solely on donor selection and donor blood screening; methods known to be useful, but insufficient. Thus, the recipients of these products must accept the risk that they may be contaminated with hepatitis viruses, HIV, cytomegalovirus or other infectious viruses. As a result, these recipients may suffer liver damage or damage to other organ systems, illness, incapacitation, and occassionally death.

Other methods for inactivation of viruses in cellular products include ultraviolet light, gamma-irradiation, or the use of beta-propiolactone. Each method can be characterized as being non-specific, modifying nucleic acid, other cell structures and proteins alike. Thus, for example, the use of ultraviolet light has been shown to inactivate viruses in a platelet concentrate, however, severe platelet damage resulted from higher intensitites. Beta-propiolactone reacts with nucleic acid and protein with similar rate constants; thus, while viruses can be activated, more than half of the factor VIII content of plasma is lost.

Yet another problem is that some of the viruses contaminating blood or other biological fluids are contained within the cell, either as a fully formed virus or in the form of free viral nucleic acid integrated into the host genome. For instance, the human immunodeficiency virus is contained within leukocytes. It is a special concern to be able to inactivate both cell-free and cell-contained forms of virus, while retaining the structure and function of cells not containing virus. Fortunately, not all viruses are contained within the cells of interest and the functionality of some cells, e.g., red blood cells or platelets, do not require cell division following transfusion.

It is to be understood that the problems of inactivation of the viruses in valuable biological mixtures are distinct from the problems of inactivation of the viruses themselves due to the copresence of the desirable proteinaceous components of the plasma. Thus, while it is known how to inactivate the hepatitis B virus by using crosslinking agents, for example, glutaraldehyde, nucleic acid reacting chemicals, for example, formaldehyde, or oxidizing agents, for example chlorox, etc., it has been believed that these methods are not suitable for the inactivation of the virus in blood due to the observation that most of these activating agents, e.g., glutaraldehyde, sodium hypochlorite or formaldehyde, denatured the valuable proteinaceous components of the plasma.

Problems may also exist in deriving valuable proteins from non-blood sources. These sources include, but are not limited to, mammalian milk, ascitic fluid, serum, saliva, placental extracts, tissue culture cell lines and their extracts, including transformed cells, and products of fermentation. For instance, the human lymphoblastoid cells have been isolated which produce alpha-interferon. However, the cell line in commercial use today contains Epstein-Barr virus genes. It has been a major concern that the use of interferon produced by these cells would transmit viral infection or induce viral caused cancerous growth.

The present application concerns the action of aryl diol epoxides to inactive viruses and simultaneously to retain labile protein activity.

Aryl diol epoxides are known to form adducts with DNA in vitro and in vivo (H. B. Gamper et al, (1980), *Proc. Nat. Acad. Sci. (USA),* 77:2000). Several studies have indicated anti-viral effects of these agents (M. L. Lockhart et al, (1986), *Chemico-Biological Interact.,* 58: 217; G. T. Chang et al, (1981), *Biochem. Biophys Res.*

Comm., 100:1337; and G. T. Bowden et al., (1986), Chemico-Biological Interact., 58:333). However, heretofore there was no indication that these compounds have been used as antiviral agents specifically in the context of the sterilization of cellular components of blood.

The present invention is directed to achieving three goals, namely, (1) a safe, (2) viral inactivated protein-containing composition, (3) without incurring substantial protein denaturation. As shown above, these three goals are not necessarily compatible since, for example, glutaraldehyde inactivates viral infectivity, but fixes cells and substances such as beta-propiolactone inactivate viruses, but also substantially denature valuable plasma proteins, for example, factor VIII.

It, therefore, became desirable to provide a virus inactivation process for obtaining cell- or protein-containing compositions which does not substantially inactivate cells or denature the valuable protein components therein. More especially, it is desirable to provide blood cell and blood protein-containing compositions in which substantially all of the hepatitis viruses and other viruses present are inactivated, but which retains at least 60% and preferably 80% intact cells, (e.g., red blood cells) and active protein (e.g., immunoglobulin).

It is a further object of the present invention to provide products from other biological fluids, from cancer or normal cells or from fermentation processes following gene insertion which are substantially free of infectious virus.

SUMMARY OF THE INVENTION

It has now been discovered that while most of the viral inactivating agents disrupt red blood cells and denature factor VIII and other valuable blood plasma proteins, that not all viral inactivating agents have such effect. It has been discovered that when a cell- or a protein-containing composition such as whole blood, red cell concentrates, platelet concentrates, leukocyte concentrates, blood cell proteins, a blood plasma protein fraction, milk, serum, semen, mammalian milk, placental extracts, products of fermentation, ascites fluid, a non-blood product produced from normal or cancerous cells (e.g., via recombinant DNA technology) is contacted for a sufficient period of time with an effective amount of an aryl diol epoxide that viruses such as the hepatitis viruses present in the composition are virtually entirely inactivated, without substantial denaturation of proteins contained therein. By contacting blood or a concentrate thereof or a fraction thereof with an aryl diol epoxide, hepatitis viruses can be substantially inactivated, e.g., to an inactivation of greater than 4 logs, while realizing a yield of intact cells as compared to total cells prior to virus inactivation and a yield of protein activity to total protein of at least 80%.

Aryl epoxide hydrolyzes to non-toxic derivatives thereof during and following the period critical to virus inactivation.

By such inventive procedures there is provided a process providing cell- or protein-containing composition such as mammalian whole blood, red cell concentrates, platelet concentrates, leukocyte concentrates, milk, semen or blood protein derivatives, having greatly reduced or vitually no hepatitis viruses or other viruses.

By the inactivation procedure of the invention, most if not virtually all of the viruses contained therein would be inactivated. A method for determining infectivity levels by in vivo chimpanzees is discussed by Prince, A. M., Stephen, W., Brotman, B. and van den Ende, M. C., "Evaluation of the Effect of Beta-propiolactone/Ultraviolet Irradiation (BPL/UV) Treatment of Source Plasma on Hepatitis Transmission by Factor IX Complex in Chimpanzees", Thrombosis and Haemostasis, 44: 138–142, (1980).

According to the invention, inactivation of virus is obtained to the extent of at least "4 logs", i.e., virus in a serum is totally inactivated to the extent determined by infectivity studies where that virus is present in the untreated serum in such a concentration that even after dilution to $10^4$, viral activity can be measured.

DETAILED DESCRIPTION OF THE INVENTION

Blood is made up of solids (cells, i.e., erythrocytes, leucocytes, and platelets) and liquid (plasma). The cells are transfused in the treatment of anemia, clotting disorders, infections, etc. In addition, the cells contain potentially valuable substances such as hemoglobin, and they can be induced to make other potentially valuable substances such as intereron, growth factors, and other biological response modifiers. The plasma is composed mainly of water, salts, lipids and proteins. The proteins are divided into groups called fibrinogens, serum globulins and serum albumins. Typical antibodies (immune globulins) found in human blood plasma include those directed against infectious hepatitis, influenza H, etc.

Blood transfusions are used to treat anemia resulting from disease or hemorrhage, shock resulting from loss of plasma proteins or loss of circulating volume, diseases where an adequate level of plasma protein is not maintained, for example, hemophilia, and to bestow passive immunization.

With certain diseases one or several of the components of blood may be lacking. Thus the administration of the proper fraction will suffice, and the other components will not be "wasted" on the patient; the other fractions can be used for another patient. The separation of blood into components and their subsequent fractionation allows the proteins to be concentrated, thus permitting concentrates to be treated. Of great importance, too, is the fact that the plasma fractions can be stored for much longer periods than whole blood and they can be distributed in the liquid, the frozen, or the dried state.

Cell types found in human blood include red blood cells, platelets and several types of leukocytes. Methods for the preparation of cell concentrates useful in transfusion can be found in *Kirk Othmer's Encyclopedia of Chemical Technology*, Third Edition, Interscience Publishers, Volume 4, pp 25–37, the entire contents of which are incorporated by reference herein.

Proteins found in human plasma include prealbumin, retinol-binding protein, albumin, alpha-globulins, beta-globulins, gamma-globulins (immune serum globulins), the coagulation proteins (antithrombin III, prothrombin, plasminogen, antihemophilic factor-factor VIII, fibrin-stabilizing factor-factor XIII and fibrinogen), immunoglobins (immunoglobulins G, A, M, D, and E), and the complement components. There are currently more than 100 plasma proteins that have been described. A comprehensive listing of such plasma proteins can be found in "The Plasma Proteins", ed. Putnam, F. W., Academic Press, New York (1975).

Blood plasma fractionation generally involves the use of organic solvents such as ethanol, ether and polyethylene glycol at low temperatures and at controlled pH values to effect precipitation of a particular fraction containing one or more plasma proteins. The resultant supernatant can itself then be precipitated and so on until the desired degree of fractionation is attained. More recently, separations are based on chromatographic processes. An excellent survey of blood fractionation appears in *Kirk-Othmer's Encylopedia of Chemical Technology*, Third Edition, Interscience Publishers, Volume 4, pages 37 to 62, the entire contents of which are incorporated by reference herein.

Proteins found in the blood cell fraction include hemoglobin, fibronectin, fibrinogen, enzymes of carbohydrate and protein metabolism, etc. In addition, the synthesis of other proteins can be induced, such as interferons and growth factors.

A comprehensive list of inducible leukocyte proteins can be found in Stanley Cohen, Edgar Pick, J. J. Oppenheim, "Biology of the Lymphokines", Academic Press, New York, (1979).

The present invention is directed to contacting one or more aryl diol epoxides with a blood cell or blood protein-containing composition such as whole mammalian blood, blood cells thereof (e.g., red blood cells, white blood cells, platelets), blood cell proteins, blood plasma thereof, single donor and apheresis derived platelets, single donor plasma, precipitates from any fractionation of such plasma, supernatants from any fractionation of such plasma, cryoprecipitate, cryosupernatant or any portion or derivatives of the above that contain blood proteins such as, for example, prothrombin complex (factors II, VII, IX and X) and cryoprecipitate (factors I and VIII).

The present invention is also concerned with contacting one or more aryl diol epoxides with a serum containing one or more blood proteins.

Furthermore, the present invention is directed to contacting one or more aryl diol epoxides with a blood protein-containing fraction containing at least one blood protein such as the following: factor II, factor VII, factor VIII, factor IX, factor X, fibrinogen and IgM.

Additionally, the present invention concerns contacting any other cell- or protein-containing composition such as a cell lysate or proteins induced in blood cells, milk, serum, semen, ascities fluid or tissue culture fluid, with one or more aryl diol epoxides.

Aryl diol epoxides for use in the present invention can be represented by the following formulas:

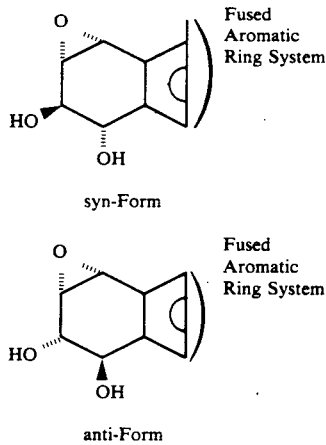

The number of rings in the aromatic ring system in the above formulas may generally range from 3 to 6.

Polycyclic aryl diol epoxides, typified by benzo (a) pyrene diol epoxide, are only sparingly soluble in aqueous media (1–10 $\mu$M). Because of their limited solubility in aqueous solutions, and their generally hydrophobic nature, these compounds can form non-covalent or physical complexes with DNA, proteins and biological membranes. Because they are hydrophobic, these compounds can also traverse cell membranes and subsequently intercalate into cellular DNA. This non-covalent binding to DNA results in the formation of DNA adducts which render the nucleic acid inactive. This same principle applies to intercalation of aryl diol epoxides into viral nucelic acids. The affinity of diol epoxides for DNA is such that extensive covalent bonding to the nucleic acid fraction occurs even in the presence of proteins to which aryl epoxides also bind noncovalently and covalently. A second important property of these molecules is that they are readily hydrolyzed in aqueous media (e.g., the half-life of benzopyrene (a) diol epoxide in Iscove's medium containing 10% fetal bovine serum is approximately 30 minutes). Thus, while the native compounds may be potentially carcinogenic, the hydrolysis products are not.

Non-limiting examples of polycyclic aryl diol epoxides for use in the present invention include trans-7,8-dihydroxy [anti] 9,10 epoxy-7,8,9,10-tetrahydro benzo[a]pyrene ("BAPDE") and analogs of BAPDE, such as, 3-methylcholanthrene diol epoxides and benzophenanthrene diol epoxides.

The physical binding of aryl diol epoxides to hydrophobic regions of proteins and biological membranes may result in an undesirable competitive reaction which may limit the extent to which these molecules react with DNA. By modifying the chemical structures of BAPDE and related molecules, their physical binding to hydrophobic cell components may be minimized, without significant affecting their chemical reactivities with DNA. In this manner, the inactivation of viruses in the presence of blood cells or other biological fluids, can be maximized.

The modification involve the synthesis of BAPDE and related compounds with side groups located on the polycyclic aromatic ring systems which will increase their water solubility, but will not markedly affect interactions with DNA. These side groups include, but are not limited to, primary amines (—NH$_2$), substituted amines (—NR$_2$, where R is an inert aliphatic alkyl chain of 1 to 3 carbon atoms), sulfonic acids (—SO$_3$—) or hydroxyalkyl derivatives having 1 to 3 carbon atoms. An example of this principle is seen in proflavin and acridine orange, two well known polynuclear aromatic molecules with —NH$_2$ and —N(CH$_3$)$_2$ side chains which bind extremely well to DNA but which are also water soluble.

The positions of substituents which impart enhanced solubility on BAPDE and related molecules on the aromatic rings can be selected to limit the effects of these side groups on binding to DNA. For example, substitution at the 2,3,4 or 5 positions of BAPDE should have a minimal effect on the reactivity with DNA, while at the same time significantly enhancing the water solubility of the molecule.

Non-limiting examples of viruses than can be inactivated by the present invention include vesicular stomatitis virus (VSV), Moloney sarcoma virus, Sindbis virus, human immunodeficiency viruses HIV-1; HIV-2), human T-cell lymphotrophic virus-I (HTLV-I), hepatitis B virus, non B, non A hepatitis virus (NANB), cytomegalovirus, Epstein Barr viruses, lactic dehydrogenase viruses, herpes group viruses, rhabdoviruses, leukoviruses, myxoviruses, alphaviruses, Arboviruses (group B), paramyxoviruses, arenaviruses and coronaviruses.

Assays of the effects of polycyclic aryl diol epoxides on the inactivation of these viruses may require the use of cell lines (e.g., A549), enzyme assays (reverse transcriptase, blood clotting times), assessment of functional, biochemical and structural integrity of cells (e.g., metabolite assays, platelet aggregometry, polyacrylamide gel electrophoresis) or the application of molecular biological techniques (e.g., infusion of animals with process cellular blood components or blood derivatives to assess infectivity, red cell survival studies, platelet survival studies).

The process of the present invention is preferably conducted at 4° to 37° C., and most preferably at 22° to 30° C. for 1 to 18 hours and preferably for 2 to 6 hours.

Preferably the concentration of the aryl diol epoxide is 1 to 500 $\mu$M, and most preferably is 1 to 10 $\mu$M.

The treatment according to the present invention is normally carried out at atmospheric pressure, although subatomospheric pressures can also be employed.

Preferred treatment conditions including following:
Reagents used: BAPDE (1–10 $\mu$M) from 1–3 mM stock in tetrahydrofuran, triethanolamine or other aprotic solvents.
Temperature: 24° C.
pH: 7.2 (6.8–7.5)
Time: 4 hours (2–6 hours)
Cell concentration:
(a) packed red cells (approximately $10^{10}$ per ml)
(b) platelet concentrate (greater than $10^{10}$ per ml)
(c) whole blood
Protein concentration:
(a) plasma (approximately 60 g/l)
(b) AHF
(c) fibronectin After treatment of cell preparation the hydrolysis products of the inactivating agent will not typically be removed. In some instances, however, (e.g., during the washing of red cells as part of freezing/thawing procedures or during the preparation of purified protein products from plasma or other sources), the hydrolysis products may be removed.

The process of the invention can be combined with still other modes of inactivating viruses. For instance, in the case of platelet concentrates, treatment with aryl diol epoxides can be supplemented by treatment with ultraviolet irradiation. Such treatment, effected with a pulsed ultraviolet (UV) laser beam, could render certain viruses inactive, without significantly impairing platelet function.

In another instance, virus inactivation in protein solutions treated with aryl diol epoxides could be supplemented with treatment with tri-N-butyl phosphate and detergents such as Tween 80 or cholic acid. Such supplemental treatments inactivate viruses, but permit retention of at least 80% of the activity of proteins such as factor VIII.

The present invention describes inactivating viruses, while simultaneously retaining labile blood cell functions and structural features, and in the case of proteins derived from blood or other sources, while retaining enzymatic, binding or other activities.

Functional activities of red cells are ascertained by measurements of metabolite levels, enzymatic activities, electrolyte levels and oxygen carring capacity. Structural integrity of red cells is assessed by measurements of osmotic fragility, survival in vivo following radiolabeling with chromium-51, antigenicity and by evaluation of modification of cell surface proteins.

Functional activities of platelets are determined by their ability to aggregate in the presence of certain biological agents, morphology and rate of fall in pH in the preparation. Structural integrity of platelets is assessed by in vivo survival following radiolabeling with indium-111 and identification of the presence of specific platelet antigens.

The activity of proteins which are enzymes is determined by measuring their enzymatic activity (e.g., factor IX).

The activity of binding proteins can be measured by determining their kinetics and affinity of binding to their natural ligands.

Lymphokine activity can be measured biologically in cell systems, typically by assaying their biological activity in cell cultures.

Protein activity generally is determined by the known and standard modes for determining the activity of the protein or type of protein involved.

In order to more fully illustrate the nature of the invention and the manner of practicing the same, the following non-limiting examples are presented:

EXAMPLES

Example 1

Vesicular stomatitis virus (VSV) was incubated, at temperatures between 4° and 30° C., in Iscove's medium containing 10% fetal bovine serum, in the presence of trans-7,8-dihydroxy [anti] 9,10, epoxy- 6,8,9,10 tetrahydro benzo[a]pyrene (BAPDE) at a concentration of 1–10 $\mu$M for 0–6 hours. Virus titer was ascertained following incubation of the supernatant suspension with A549 cells; virus kill was inversely proportional to the appearance of cytopathology in the cell cultures. BAPDE effectively inactivated in excess of 5 logs of virus under these conditions compared to controls in which BAPDE was omitted. Neither BAPDE nor the solvent in which it was dissolved (e.g., tetrahydroturan) were toxic to A549 cells under these conditions.

Example 2

In a second series of experiments, VSV was exposed to BAPDE under the same experimental conditions in Example 1, except that washed human red blood cells were added at concentrations between $10^4$ and $10^9$ cells/ml. VSV inactivation was reduced in the presence of red cells, but the virus titer was reduced at least 3 logs relative to controls in which BAPDE was omitted.

Red cell structural and functional integrity was not compromised under the experimental conditions described. Measurements of osmotic fragility, hemoglobin content, ATP levels and 2,3 diphosphoglycerate levels were all within the normal range.

Example 3

The preceding examples illustrate the BAPDE can effectively kill virus which is free in suspension in the presence of red cells. An equally important application is the inactivation of viruses which have become cell-associated or incorporated into target cells.

VSV ($10^6$ infectious units) was incubated with A549 cells for 6 hours at 37° C. During this period, the virus was taken up by the cells and entered a replicative cycle. The cells were washed extensively to remove non-cell associate virus, removed from the tissue culture plates and suspended in Iscove's medium containing 4% fetal bovine serum. The cells were exposed to BAPDE at 3 μM. The preparation was incubated at 24° C. for 0-6 hours and virus titer assessed by assay on fresh A549 cells. BAPDE effected greater than 5.5 logs of virus kill under these conditions compared to control preparations from which BAPDE was omitted.

Example 4

Human plasma was incubated with BAPDE at a concentration of 10 μm for 6 hours at 24° C. Prior to incubation, VSV was added to the plasma to serve as a marker of virus kill. The functional activity of selected plasma proteins and the infectivity of VSV was assessed prior to and following incubation with BAPDE. The results in the accompanying Table indicate virus inactivation to the extent of greater than 4.5 $\log_{10}$ without significant loss of protein functional activity.

TABLE I

|  | NO TREAT-MENT | FOLLOWING TREATMENT with BAPDE | CHANGE |
| --- | --- | --- | --- |
| VSV Infectivity (log ID$_{50}$) | 4.1 | <−0.5 | log$_{10}$ Kill >4.6 Recovery (%) |
| Anti-HBsAg (titer) | 0.50 | 0.55 | 110% |
| Fibrinogen clottability | clottable | clottable | 100% |
| AHF (units/ml) | 0.70 | 0.55 | 79% |
| Factor IX (units/ml) | 0.9 | 0.9 | 100% |
| Haptoglobin (mg/dl) | 175 | 170 | 97% |

It will be appreciated that the instant specification and claims are set forth by way of illustration and not limitation, and that various modifications and changes may be made without departing from the spirit and scope of the present invention.

What is claimed is:

1. A process of inactivating infectious viruses in a cell-containing or a protein-containing composition containing such viruses, comprising contacting such composition with an effective amount of at least one aryl diol epoxide of the formula

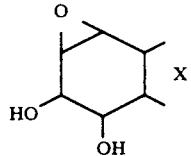

in which

X is an aromatic ring system having from 3 to 6 fused rings, for a sufficient period of time substantially to inactivate said viruses without incurring substantial disruption or inactivation of cells or without incurring substantial protein denaturation.

2. A process according to claim 1, wherein X includes at least one side group selected from the group consisting of primary amines, substituted amines of the formula —NR$_2$ where R is an aliphatic alkyl chain of 1 to 3 carbon atoms, sulfonic acids and hydroxyalkyl derivatives having 1 to 3 carbon atoms.

3. A process according to claim 2, wherein the aryl diol epoxide is selected from the group consisting of trans-7,8-dihydroxy [anti] 9,10, epoxy-7,8,9,10 tetrahydro benzo[a]pyrene, methylcholanthrene diol epoxides and benzophenanthrene diol epoxides.

4. A process according to claim 2, wherein the contacting is conducted at a temperature of 4° to 37° C.

5. A process according to claim 2, wherein the contacting is conducted at a temperature of 22° C. to 30° C.

6. A process according to claim 2, wherein the contacting is conducted for a time of 1 to 18 hours.

7. A process according to claim 2, wherein the contacting is conducted for a time of 2 to 6 hours.

8. A process according to claim 2, wherein the contacting is conducted at a pH of 6.8 to 7.5.

9. A process according to claim 2, wherein the aryl diol epoxide is at a concentration of 1 to 500 μM.

10. A process according to claim 2, wherein the concentration is 1 to 10 μM.

11. A process according to claim 2, wherein said protein-containing composition is selected from the group consisting of whole mammalian blood, blood cell proteins, milk, saliva, blood plasma, a plasma concentrate, a precipitate from any fractionation of said plasma, a supernatant from any fractionation of said plasma, a serum, a cryoprecipitate, a cryosupernatant, a cell lysate, placental extracts and products of fermentation.

12. A process according to claim 2, wherein said cell-containing composition includes one or more components selected from the group consisting of red blood cell concentrates, platelet concentrates, leukocyte concentrates, semen, ascitic fluid, hybridoma cell lines and whole mammalian blood.

13. A process according to claim 2, wherein said composition is the product of a non-blood normal or cancerous cell or the product of gene splicing.

14. A process according to claim 2, further comprising heat treating the composition.

15. A process according to claim 2, further comprising contacting the composition with solvents, detergents or solvents and detergents.

* * * * *